United States Patent
Schulz

(10) Patent No.: US 9,883,902 B2
(45) Date of Patent: Feb. 6, 2018

(54) SURGICAL DEVICE WITH IMPROVED MAINS MODULE

(71) Applicant: ERBE ELEKTROMEDIZIN GMBH, Tuebingen (DE)

(72) Inventor: Florian Schulz, Rottenburg a.N. (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 686 days.

(21) Appl. No.: 14/502,618

(22) Filed: Sep. 30, 2014

(65) Prior Publication Data

US 2015/0133912 A1    May 14, 2015

(30) Foreign Application Priority Data

Sep. 30, 2013 (EP) ..................... 13186749

(51) Int. Cl.
*A61B 18/00* (2006.01)
*A61B 18/12* (2006.01)

(52) U.S. Cl.
CPC .......... *A61B 18/1206* (2013.01); *A61B 2018/00702* (2013.01); *A61B 2018/1286* (2013.01)

(58) Field of Classification Search
CPC ......... H03L 1/00–1/04; A61B 18/1206; A61B 2018/00702; A61B 2018/1286; H02M 1/10; H02M 2001/0003; H02M 3/00
See application file for complete search history.

(56) References Cited

U.S. PATENT DOCUMENTS

| 4,860,745 A | 8/1989 | Farin et al. |
| 2012/0083779 A1 | 4/2012 | Hosier |

FOREIGN PATENT DOCUMENTS

| CN | 101572484 A | 11/2009 |
| CN | 201489092 U | 5/2010 |
| DE | 10 2004 010 769 A1 | 9/2005 |
| DE | 11 2009 001 250 T5 | 4/2011 |
| EP | 0 430 929 A2 | 6/1991 |
| EP | 1 519 472 A1 | 3/2005 |
| JP | 63-24933 A | 2/1988 |
| JP | 2001-37774 A | 2/2001 |
| JP | 2005-536314 A | 12/2005 |
| JP | 2010-527676 A | 8/2010 |
| WO | WO 2004/030552 A1 | 4/2004 |
| WO | WO 2008/142404 A1 | 11/2008 |
| WO | WO 2010/124785 A1 | 11/2010 |

*Primary Examiner* — Scott Getzow
(74) *Attorney, Agent, or Firm* — Blank Rome LLP

(57) ABSTRACT

A surgical device having a step-up converter, a power supply unit and a control arrangement. The step-up converter converts a mains AC voltage to an intermediate circuit voltage and energizes a DC intermediate circuit. The power supply unit includes an inverter connected to the intermediate circuit. The power supply unit also includes a transformer that has a primary coil connected to the inverter and a secondary coil for energizing a load. The control arrangement includes a PFC control circuit connected in a controlling manner to the step-up converter. The control arrangement further includes an operation control circuit connected in a controlling manner to the power supply unit. The PFC control circuit and operation control circuit are connected to each other via a digital communication interface.

15 Claims, 3 Drawing Sheets

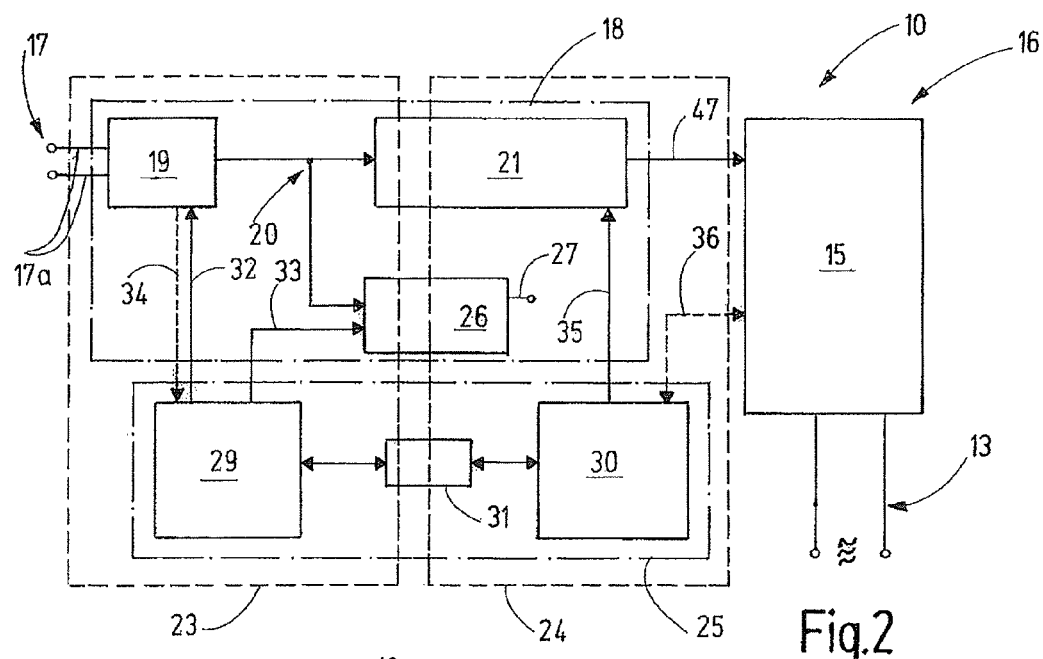
Fig.2
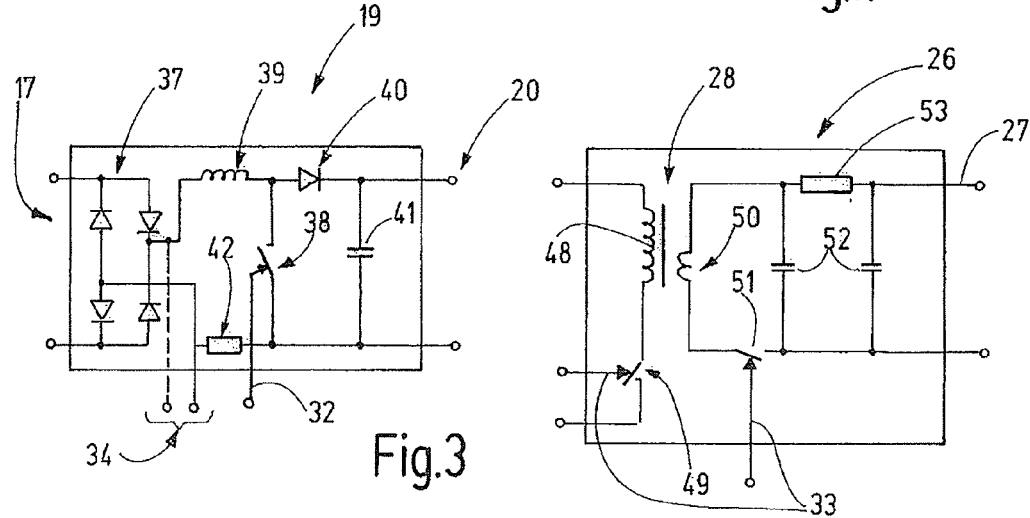
Fig.3
Fig.4
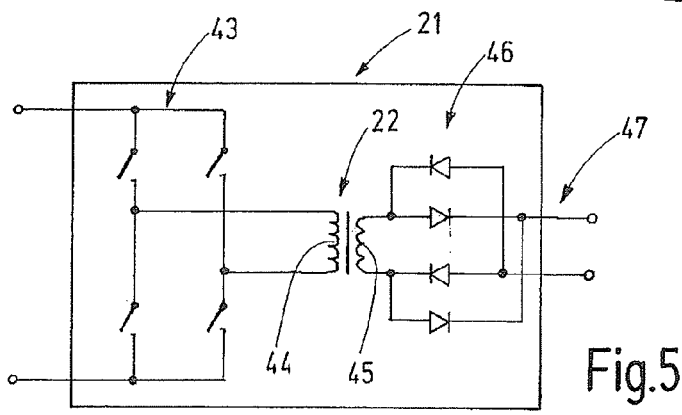
Fig.5

SURGICAL DEVICE WITH IMPROVED MAINS MODULE

TECHNICAL FIELD

Embodiments of the invention relate to a surgical device, in particular a radio frequency (RF) surgical device for supplying a surgical instrument.

BACKGROUND

Electrosurgical devices usually comprise a power supply unit that supplies the device with electrical power from the public power supply system.

In conjunction with this, publication DE 11 2009 001250 T5 discloses a device comprising a power supply unit including adjustable inverters for energizing RF generators. The RF generator is disposed for the simultaneous output of different RF output voltage waveforms. Alternatively, these are disposed for cutting or coagulation. The device is controlled by a central component with a user interface, wherein this central component controls the power supply unit as well as the RF generator. In doing so, the power supply unit can be controlled by means of events that occur in the RF circuit in order to thus increase or decrease the circuit's voltage. To do so, the central control component sends a corresponding direct-current request to the power supply unit.

Considering this, it is the object of the disclosed embodiments to provide a concept for an electrosurgical device with an improved systems architecture.

SUMMARY

The electrosurgical device in accordance the disclosed embodiments provides an operating voltage that is electrically insulated with respect to the mains power supply for a load such as, e.g., an RF generator, by means of a step-up converter and a downstream power supply unit. A control arrangement acts in a controlling manner on the step-up converter as well as on the power supply unit. The step-up converter effects a power factor correction (PFC). It is disposed to take the closest possible sinusoidal current from the power supply network and generate a direct voltage therefrom (intermediate circuit voltage). The intermediate circuit voltage is converted into a voltage for supplying the load, i.e., for example the RF generator. The step-up converter is controlled by a PFC control circuit. The power supply unit is controlled by an operation control circuit. The PFC control circuit and the operation control circuit are connected to each other via a digital communication interface. Together, the PFC control circuit, the power supply unit and the digital communication interface form the control arrangement.

The first and foremost task of the operation control circuit is the control of the load, i.e., for example the RF generator and the associate power supply unit. In contrast, the first and foremost task of the PFC control circuit is the control of the step-up converter. Preferably, the PFC control circuit can also control a low voltage supply unit that—like the power supply unit—is connected to the intermediate circuit voltage. The low voltage power supply unit is disposed for generating a low voltage, for example 12 V, that is electrically insulated from the voltage supply network.

The digital communication interface between the PFC control circuit and the operation control circuit allows a data exchange between the two, in which case the PFC control circuit and the operation control circuit operate otherwise autonomously. The PFC control circuit comprises, for example, a microcontroller or another control arrangement that is preferably configured so that it is programmable. This may comprise programmable regulating properties. This may include a programmable transient response, an adjustable power limit as well as the undervoltage detection and also the switching of components. Components that can be switched depending on the input voltage are, in particular, inductive storage elements of the step-up converter. The undervoltage detection, the overvoltage detection, the overcurrent detection or the like can be used for the generation of signals.

The digital communication interface allows the reporting of such events (undervoltage, overvoltage, overcurrent and the like) by the transmission of signals (event signals) by the PFC control circuit to the operation control circuit. In this manner, it is possible, for example, to inform the operation control circuit of a mains power failure before the intermediate circuit voltage drops significantly. In response thereto, it can switch off all bigger energy consumers (load, display, fans and the like) and use the residual energy for saving data, for example on the buffer capacitors of the intermediate circuit, and convert active controllers into a defined non-operative mode.

The PFC control circuit and the operation control circuit are preferably designed so as to be spatially separate. In doing so, they may be mounted to a board or also be provided in different components. The spatial and functional separation of the PC control circuit from the operation control circuit allows a simple galvanic separation and a special adaptation of the PFC control circuit to the tasks in the control of the step-up converter and, potentially, a low voltage power supply unit while the operation control circuit can be optimized in view of the control of the load and the power supply unit. Consequently, the PFC control circuit and the operation control circuit can be provided, for example, as modules for various application and power classes and can individually be connected by the digital communication interface. This creates simple adaptation and design options for the assembly of various power supply units for various tasks with the use of standardized modules.

The load may be an RF generator that can be operated in different operating modes with different power consumption. For example, the power consumption of the load and the RF voltages to be generated by said load are typically greater for cutting than for coagulating operations. The operation control circuit can control the load, i.e., the RF generator, in order to trigger different operating modes. At the same time, the operating control circuit is able to adapt the power supply unit to different operating modes in that, for example, it is adjusted to different desired voltages (e.g., 5 V-250 V, depending on whether a coagulating or cutting operation is to be performed). At the same time (or beforehand), the control circuit can output a signal to the PFC control circuit in order to adapt said circuit to different wattages. In doing so, regulating processes that would otherwise occur in the case of load surges for maintaining the intermediate circuit voltage at a constant level are avoided or clearly shortened. In doing so, the PFC control circuit can be controlled in an anticipatory manner. In particular, it is useful if the operation control circuit is configured in such a manner that it outputs a signal via the digital communication interface to the PFC control circuit, before switching the operating mode, in order to adjust said control circuit to the impending changed power consumption of the load. In doing so, it can be ensured that the energy required for the start of the cutting operation is in actuality provided and made available in the intermediate circuit.

As mentioned, the PFC control circuit can additionally control a potential-separating DC-DC converter. Preferably, this converter may be configured as a blocking converter. Furthermore, preferably, this blocking converter comprises a synchronous rectifier. The PFC control circuit can control the primary-side electronic switch of the blocking converter as well as the synchronous rectifier. By depositing appropriate characteristics and timing schematics in the PFC control circuit it can be achieved that the blocking converter and the connected synchronous rectifier operate over a wide load range with an increased degree of efficacy and, in addition, that the electronic primary-side switch is safely switched in the event of zero current crossings. The same applies to the electronic switch of the synchronous rectifier.

In the method herein, the operation control circuit can send a signal to the PFC control circuit via the communication interface before a load change in order to adapt the operation of the step-up converter to the impending change of the power requirements of the load. This improves the operating behavior of the power supply unit and an RF generator or any other load connected thereto. Also, data yielded in the step-up converter can be reported to the operation control circuit in order to affect the orderly powering-down of the surgical device, for example, without any loss of measured data, settings and parameters.

In stationary operating mode, the PFC control circuit 29 can be supplied with operating voltage via the output of the low voltage power supply unit. However, the latter power supply unit is itself controlled by the PFC control circuit so that—in order to speed up the powering-up or make it possible at all—a starting circuit may be provided. Preferably, said starting circuit comprises at least one electronic switch that clears a resistive current path from the direct current (DC) intermediate circuit to the operation voltage input of the PFC control circuit until the low voltage supply unit reliably supplies the operating voltage. As soon as this is the case the starting circuit becomes inactive. Consequently, ohmic losses on its current path to the temporary supply are minimized.

Further details of advantageous embodiments of the invention are the subject matter of the description, claims and/or the drawings.

BRIEF DESCRIPTION OF THE DRAWINGS

FIG. 2 is a block circuit diagram of the surgical device as in FIG. 1;

FIGS. 3 to 6 are schematized circuit diagrams of components of the surgical device shown in FIGS. 1 and 2.

DETAILED DESCRIPTION

Figure 1:
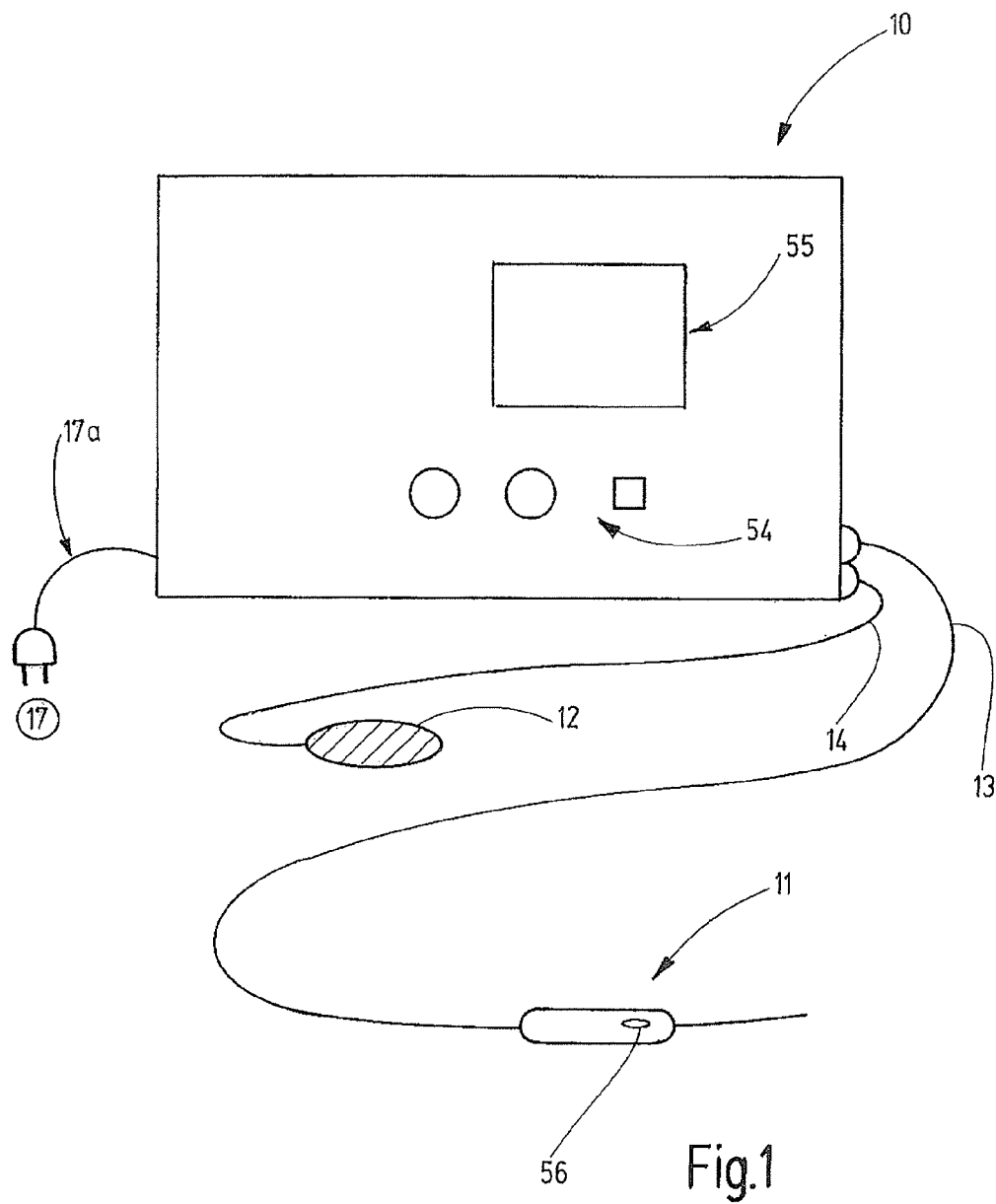
FIG. 1 is a schematic comprehensive illustration for energizing a surgical instrument.

FIG. 1 shows a surgical device 10 for energizing a surgical instrument 11. The instrument 11 may be an instrument for use in open surgery or it may be an instrument for laparoscopic use. The instrument may be monopolar as shown, in which case a neutral electrode 12 must be attached to the patient or object to be treated. The instrument 11 may also be bipolar. In this case, no neutral electrode 12 is needed, and the instrument 11 is supplied with power via a two-wire line. The instrument 11 and the neutral electrode 12 are connected to the surgical device 10 via lines 13, 14 in order to be supplied with current and optionally other media such as, for example, rinsing fluid or the like.

In order to energize the instrument 11, the surgical device 10 comprises, for example, an RF generator 15 that can be seen in the block circuit diagram of FIG. 2. Together with the connected instrument 11 of the patient located in the electrical circuit, said generator forms an electrical load 16. The electrical power required for operating this load 16 is derived from a power supply network 17 to which the surgical device 10 is connected via a power cable 17a. Between the load 16 (or the generator 15) and the power supply network 17 connected via the power cable 17a, there is interposed a power supply section 18 that provides the operating voltage necessary for the load 16 and the necessary operating current. In addition, the power supply section 18 accomplishes an electrical isolation between the load 16 and the power supply network 17.

FIG. 2 shows the major assemblies of the surgical device 10. The power supply section 18 comprises a step-up converter 19 for power factor correction. Via the power cable 17a, the step-up converter 19 takes electrical current from the power supply network 17 and energizes a DC intermediate circuit 20 with a direct voltage of desired intensity, this being preferably greater than the peak value of the supplied mains voltage (e.g., 400 V). Connected to the DC intermediate circuit 20 is a power supply unit 21 that is disposed for supplying the load 16 with a suitable voltage, said voltage preferably being adjustable within a wide adjustment range of, e.g., 5 to 250 Volts.

The power supply unit 21 is schematically shown by FIG. 5. It comprises a transformer 22 that is disposed for the electrical isolation and hence allocates the power supply section 18 to a first mains-side region 23 carrying a mains voltage and a patient-side second region 24 separate from the mains voltage. The two regions 23, 24 comprise the power supply section 18 as well as a control arrangement 25.

The power supply section 18 comprises, at least optionally, a low voltage power supply unit 26 that is connected to the DC intermediate circuit 20 on the input side and that makes available, at its output 27, a suitable low voltage of 12 V, for example. The low voltage power supply unit 26 is shown separately by FIG. 4. The latter, again, comprises a transformer for electrical isolation, so that one part of the low voltage supply unit 26 and of the power supply unit 21 belongs to the mains-side region 23 and the other part belongs to the patient-side region 24.

The same is true of the control arrangement 25. It comprises a PFC control circuit 29 located in a mains-side region 23. Furthermore, the control arrangement 25 comprises an operation control circuit 30 located in the patient-side region 24. The PFC control circuit 29 and the operation control circuit 30 are connected to each other via a digital communication interface 31 that is preferably bidirectionally electrically insulating.

The PFC control circuit 29 also controls the operation of the step-up converter 19, if any, and also the operation of the low voltage power supply unit 26. These causal relationships are indicated by arrows 32, 33 in FIG. 2. Furthermore, as indicated by arrow 34, the mains-side region 23 of the power supply section 18, for example the step-up converter 19, can output information to the PFC control circuit 29.

As symbolically indicated by arrow 35, the control operation control circuit 30 controls at least the power supply unit. Furthermore, the operation control circuit 30 may be disposed so as to be able to control the load 16 as well as receive information from the load 16, as indicated by arrow 36. For control of the load 16, the operation control circuit 30, for example, may prespecify the operating modes such as, for example, cutting or coagulation. For example, the operation control circuit 30, can receive information via voltages and/or currents on the input side or the output side of the generator 15.

FIG. 3 describes one embodiment of the step-up converter 19, this description being restricted to its basic components. A power rectifier 37 is provided on the input side. Downstream thereof is a series circuit composed of an electronic switch 38 and an inductive component 39. The control electrode of the electronic switch 38, said electrode for example being configured as a MOSFET, receives control pulses via the line of the PFC control circuit 29, as indicated by arrow 32. On the output side, the step-up converter comprises a rectifier diode 40 and a buffer capacitor 41. At a suitable point, a mains voltage signal can be tapped and delivered to the PFC control circuit 29. Furthermore, a shunt 42 may be provided at a suitable location, the voltage drop of said shunt also being delivered to the PFC control circuit 29 (arrow or tap 34 in FIG. 3). On its output, the step-up converter 19 energizes the DC intermediate circuit 20.

The power supply unit 21 as in FIG. 5, as well as, optionally, the low voltage power supply unit 26 as in FIG. 4 are connected to the DC intermediate circuit 20.

The power supply unit 21 comprises an inverter 43, preferably configured as a full bridge inverter. The latter comprises four electronically controllable switches that are controlled, via an operative connection 35, by the operation control circuit 30. Connected to the inverter 43 is the primary coil 44 of the transformer 22. Its secondary coil 45 is connected to the rectifier block 46, whose output 47 supplies the load 16 with a direct voltage of, e.g., 5 to 250 V. As illustrated, the rectifier block 46 may be composed of a diode bridge circuit or also, of a foreign-controlled switch, as a synchronous rectifier. The degree of the direct voltage can preferably be controlled by the appropriate control of the inverter block 43 by the operation control circuit 30.

The low voltage power supply unit 26 that is intended for lower power levels is preferably a flyback converter circuit. The primary coil 48 of the transformer 28 is connected in series to an electronic switch 49. The control electrode of the electronic switch 49 is connected to the PFC control circuit 29 via suitable pulse transmission means. The secondary coil 50 of the transformer 28 is connected to one or more buffer capacitors 52 via an electronic switch 51, whereby a screen resistor 53 or also an appropriate choke may be interposed between said buffer capacitors. The control electrode of the electronic circuit 51 is controlled by the PFC control circuit 29 via the operative connection indicated by event 33.

The PFC control circuit 29 may be a microcontroller that adapts the timing of the switching-on and switching-off operations of the electronic circuit 49, 41 in such a manner that the switch 51 is configured as a synchronous rectifier.

Figure 6:
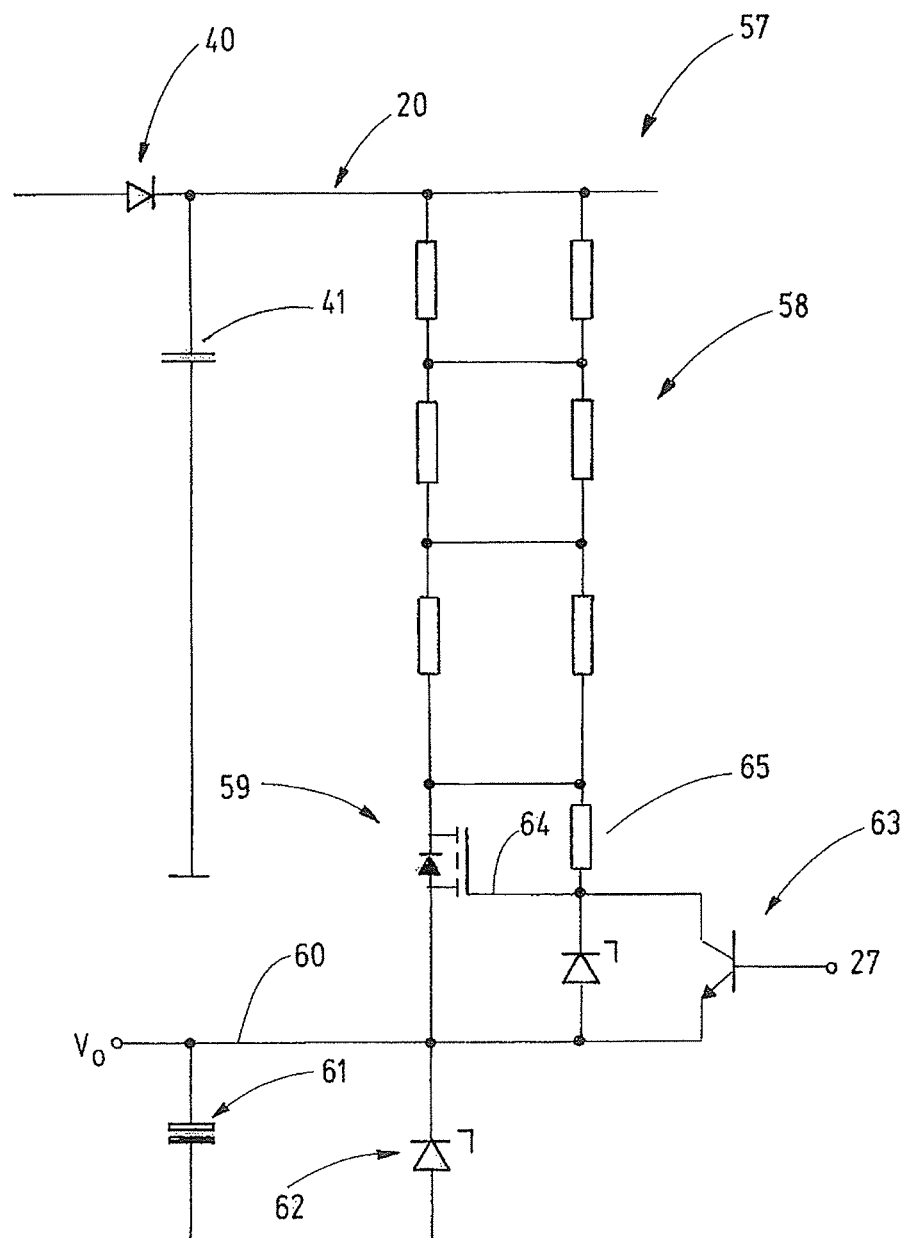

FIG. 6 shows a starting circuit 57 that is disposed to supply the PFC control circuit 29 after the start with operating voltage until the low voltage power supply unit 26 works in a stable manner. In doing so, the starting circuit 57 is connected to the DC intermediate circuit 20. From there, extends at least one ohmic resistor, preferably a resistor chain 58 to an electronic switch 59. The series circuit composed of the resistor chain 58 and the electronic switch 59 defines a current path from the DC intermediate circuit 20 to a line 60 conducting a low voltage, said line being connected to the operating voltage input VO of the PFC control circuit 29. By means of a capacitor 61, the line 60 is buffered to ground. For voltage limitation, the capacitor 61 is bridged by a Zener diode 62.

The line 60 conducting the low voltage is connected to the output 27 of the low voltage supply unit 26 via a supply current path. In the present exemplary embodiment, the supply current path is composed of the base emitter diode or one or more parallel-connected transistors, preferably npn transistors 63. The supply current path forms the control input for the electronic switch 59. As soon as sufficient electrical current flows in the supply current path, the electronic switch 59 moves into its OFF position. In the exemplary embodiment, the electronic switch 59 is a field effect transistor whose gate 64 is connected to the collector of the transistor 63, as well as to the resistor chain 58 via a pull-up resistor 65. Furthermore, its gate may be connected to its source connection via a voltage-limiting Zener diode. If its gate 64 is sufficiently positive relative to its source connection, the field effect transistor is conductive. It is blocking if the gate 64 is at or near the source potential.

Additional properties of the circuit of the surgical device 10 described so far in view of its structure and basic architecture result from the functional description hereinafter.

The components and blocks of the surgical device are configured in such a manner that the function described hereinafter is provided or can be provided:

To begin with, it is assumed that the operation of the surgical device 10 has been started up.

At the start, due to absent control pulses from the PFC control circuit 29 and the operation control circuit 30, neither the two step-up converters nor power supply unit 21, nor the low voltage supply unit 26 can operate. Via the diode 40, the buffer capacitor 41 receives rectified mains half-waves and thus charges to a voltage that is initially lower than the desired intermediate circuit voltage. Now the starting circuit 57 will activate in that a positive voltage reaches the gate 64 via the resistor chain 58 and the pull-up resistor 65. Consequently, the switch 59 becomes conductive (ON), as a result of which a charge current limited by the resistor chain 58 flows to the capacitor 61, charging said capacitor. The building voltage is limited by the Zener diode 62. Consequently, the initial operation of the PFC control circuit 29 is made possible. The latter can now send control pulses to the step-up converter 19, as a result of which it begins operating and building the desired intermediate circuit voltage on the capacitor 41. At the same time, the low voltage power supply unit 26, under the control of the PFC control circuit 29, can start its operation and make available the desired and required voltage at its output 27. An electrical supply current flows across the base-emitter diode of the transistor 63 to the line 60, as a result of which the collector-emitter path of the transistor 63 becomes conductive. The gate 64 of the field effect transistor is thus pulled to source potential. In any event, the gate-source voltage drops below the threshold voltage of the field effect transistor, hence said transistor will block (OFF). As a result of this, the resistor chain 58 will be without electrical power output and without power loss. In doing so, the stationary mode of the PFC control circuit 29 has been reached. On the one hand, the resistor chain can thus be designed to be relatively low-ohmic in order to allow at once a fast start and satisfy the high power requirement of the PFC control circuit, in which case, on the other hand, the power loss occurring during operation is minimized by the automatic power off.

Now the step-up converter 19 converts the wavy rectified mains voltage into a direct voltage of, e.g., 400 V. To do so, the electronic switch 38 is opened and closed by the PFC control circuit 29 at a frequency clearly above the mains frequency. There may be the provision that the PFC control circuit 29 monitors the voltage in the DC intermediate circuit 20 and thus regulates the duty cycle of the switch 38 in such a manner that the desired direct voltage is maintained.

It is now assumed that the operation control circuit 30 must prespecify a specific operation of the instrument 11, for example, coagulation mode. This mode may be selected, for example, by one or more control elements 54 on the housing of the surgical device 10 and be signaled by one or more display arrangements. Furthermore, the display arrangement 55 may be disposed to indicate additional parameters such as electrical power, voltage, duration of coagulation or the like.

If the user now employs the instrument at the application site and actuates, for example, a control element 56 on the handle of the instrument 11, the generator 15 must be activated, for example. Prior to that, the operation control circuit 30 adjusts the power supply unit 21 by operative connection 35 in such a manner that the voltage required for coagulation is applied. This is accomplished by appropriate clocking of the switch of the inverter 43. By means of the operational connection 36, it is possible to activate the generator 15 and to monitor its parameters, e.g., the level of the electrical current and/or the level of the output voltage. The RF generator 15, the operation control circuit 30 and the power supply unit 21 can thus form a control loop in order to maintain the desired parameters in a controlled manner or to control them consistent with prespecifiable functions.

The operation control circuit 30 can also control other operating modes, for example, cutting mode with initial incision in a moist environment. This requires increased power. While the operation control circuit 30 regulates the voltage at the output 47 by influencing the power supply unit 21, it can report the impending increased electrical power requirement to the PFC control circuit 29 via the communication interface 31. Said control circuit can be designed so as to increase the input current measured via the shunt 42 for a short time. To do so, the PFC control circuit deviates from its otherwise taken up operation of maintaining the voltage constant in the DC intermediate circuit 20. This is normally adjusted constantly in that the voltage is measured and compared with a nominal value by the PFC control circuit 29. A nominal electrical power value will be calculated based on the voltage difference, said nominal value being compared with the electrical current actually measured on the shunt 42. In stationary mode, the switch 38 is activated in such a manner that the actual current corresponds to the nominal current.

In anticipation of and preparation for a transient process, in particular a surge-like increase of the power requirement of the load 16, the PFC control circuit 29 can add an offset to the nominal electrical power value and maintain it for a given or selected time. As a result of this, the step-up converter 19 conveys more energy into the DC intermediate circuit 20, said energy now being available for the power supply unit 21 and the load 16, for example, in order to perform an initial cutting operation.

In this configuration, it is possible to act in an anticipatory manner to impending load changes. As a result of this, voltage drops that could otherwise occur in the DC intermediate circuit 20 and would have to be compensated for by voltage regulation if the response were only to load surges are avoided.

Beyond that, the communication interface 31 between the PFC control circuit 29 and the operation control circuit 30 allows additional advantageous behavior of the surgical device 10. For example, in the case of a mains failure at the mains line 17, this can be reported immediately to the PFC control circuit 29 via the operational connection indicated by arrow 34 and by said control circuit to the operation control circuit 30 via the communication interface 31. A possible response in such a case is that the operation control circuit 30 immediately shuts down the power supply unit 21 in order to allow the longest possible continued operation of the low voltage power supply unit 26 with the energy stored on the buffer capacitor 41 in the DC intermediate circuit 20, for example. The continued operation of the low voltage power supply unit 26 for at least fractions of a second or also several seconds makes it then possible to store data and setting values on not specifically illustrated components such as, in particular, memories and computing components and to complete the operation in an orderly manner. In contrast, energy-consuming components such as, in particular, the display arrangement 55, the load 16 or the like, are shut off instantly.

The surgical device 10 in accordance with embodiments of the invention includes a power supply section 18 comprising at least one step-up converter 19 and at least one power supply unit 21. The step-up converter 19 or, preferably, the power supply unit 21 effects an electrical insulation. A DC intermediate circuit 20 is provided between the two. The step-up converter 19 is driven by a dedicated PFC control circuit 29. As opposed to this, the power supply unit 21 is driven by the operation control circuit 30 that controls the general operation of the surgical device 10. Provided between the PFC control circuit 29 and the operation control circuit 30 is a digital communication interface 31 by way of which the operation control circuit 30 can receive additional data from the step-up converter 19 or pass said data on to said step-up converter. In so doing, a particularly fast and safe response is possible in case of a mains power failure. Furthermore, the step-up converter can be operated in an anticipatory manner in anticipation of impending load changes. As a result of this, it is possible to improve the operating properties of the surgical device 10, for example in view of the initial incision.

What is claimed as new and desired to be protected by Letters Patent of the United States is:

1. A surgical device, in particular a RF surgical device for supplying a surgical instrument, comprising:
    a DC intermediate circuit;
    a step-up converter that is disposed to convert a mains AC voltage to an intermediate circuit voltage and to energize the DC intermediate circuit;
    a power supply unit comprising an inverter connected to the DC intermediate circuit, and comprising a transformer comprising a primary coil connected to the inverter and a secondary coil for energizing a load:, and
    a control arrangement comprising a PFC control circuit connected in a controlling manner to the step-up converter and an operation control circuit connected in a controlling manner to the power supply unit, the PFC control circuit and the operation control circuit being connected to each other via a digital communication interface.

2. The surgical device of claim 1, wherein the operation control circuit is furthermore connected to the load in a controlling manner.

3. The surgical device of claim 2, wherein the load can he driven in different operating modes in which said load exhibits different power consumptions.

4. The surgical device of claim 2, wherein the operation control circuit is configured to prespecify the operating mode of the load and that the operation control circuit is further configured to control the power supply unit and the PFC control circuit consistent with the operating mode of the load.

5. The surgical device of claim 4, wherein the operation control circuit is configured to adjust the power supply unit, before switching the operating mode, to the impending changed power consumption of the load.

6. The surgical device of claim 4, wherein the operation control circuit is configured so as to adjust the PFC control circuit, before switching the operating mode, to the impending changed power consumption of the load via the digital communication interface.

7. The surgical device of claim 1, wherein the digital communication interface is configured so as to be electrically isolating.

8. The device of claim 1, wherein the digital communication interface is configured so as to operate bidirectionally.

9. The surgical device of claim 1, wherein a low voltage power supply unit is connected to the intermediate circuit, said low voltage power supply unit being an electrically isolating DC-DC converter.

10. The surgical device of claim 9, wherein the electrically isolating DC-DC converter comprises a flow converter or blocking converter with a synchronous rectifier.

11. The surgical device of claim 9, wherein the low voltage power supply unit is controlled by the PFC control circuit.

12. The surgical device of claim 10, wherein the flow or blocking converter comprises at least one electronic switch that is connected in series to a primary coil of an electrically isolating transformer, in which case the switch is clocked by the PFC control circuit.

13. The surgical device of claim 10, wherein the synchronous rectifier comprises an electronic switch with a control electrode into which are input switching pulses that are generated by the PFC control circuit.

14. The surgical device of claim 1, wherein the PFC control circuit is connected to the DC intermediate circuit via an automatic power-off starting circuit.

15. A method for providing an electrical operating power for a load, in particular an RF generator, for supplying a surgical instrument, the method comprising:
    energizing an intermediate circuit by a step-up converter converting a mains AC voltage to an intermediate circuit voltage;
    energizing the load by a power supply unit that is supplied with electrical energy from the intermediate circuit; and
    supplying a PFC control circuit via a digital communication interface with control signals that originate from an operation control circuit and characterize load changes, the PFC control circuit being connected in a controlling manner to the step-up converter and sending status signals to the operation control circuit.

\* \* \* \* \*